United States Patent [19]
Carli et al.

[11] Patent Number: 6,107,276
[45] Date of Patent: Aug. 22, 2000

[54] PHARMACEUTICAL COMPOSITIONS INCLUDING A DRUG, A CROSS-LINKED POLYMERIC SUBSTANCE, AN OIL, AND A SURFACE ACTIVE AGENT

[75] Inventors: Fabio Carli; Daniela Lombardi; Pierandrea Esposito; Luca Dobetti; Luigi Boltri, all of Trieste, Italy

[73] Assignee: Vectorpharma International S.p.A., Trieste, Italy

[21] Appl. No.: 08/997,463

[22] Filed: Dec. 23, 1997

Related U.S. Application Data

[63] Continuation of application No. 08/528,597, Sep. 15, 1995, which is a continuation of application No. 08/150,227, Nov. 10, 1993, abandoned.

[30] Foreign Application Priority Data

Nov. 13, 1992 [IT] Italy .................................. MI92A2603

[51] Int. Cl.⁷ .......................... A01N 35/00; A01N 43/82; A61K 31/56; A61K 38/00

[52] U.S. Cl. ........................... 514/11; 514/689; 514/357; 514/181; 514/177; 514/32

[58] Field of Search .................................. 514/689, 357, 514/181, 177, 32, 11

[56] References Cited

U.S. PATENT DOCUMENTS 4,755,385  7/1988  Etienne et al. ........................... 424/154

OTHER PUBLICATIONS

Lippold et al 89CA 186000R, 1978.
Lovrecich 113 CA 138530P, 1990.
Sarpotdar et al 106 CA 143898s, 1987

*Primary Examiner*—Russell Travers

[57] ABSTRACT

The pharmaceutical compositions including a slightly soluble drug incorporated in a water-swellable, but water-insoluble cross-linked polymer, a surface active agent, and an oil show much improved dissolution and, consequently, bioavailability in respect of the drug as is or used with a polymeric carrier of said type.

4 Claims, 6 Drawing Sheets

PHARMACEUTICAL COMPOSITIONS INCLUDING A DRUG, A CROSS-LINKED POLYMERIC SUBSTANCE, AN OIL, AND A SURFACE ACTIVE AGENT

This is a continuation of application Ser. No. 08/528,597, filed Sep. 15, 1995, which is a continuation os application Ser. No. 08/150,227 now abandoned, filed Nov. 10, 1993, which, claims priority for Italian Patent Application Serial No. MI92A002603.

FIELD OF THE INVENTION

The present invention contemplates pharmaceutical compositions including slightly soluble drugs and cross-linked polymeric carriers.

PRIOR ART

Several drugs for oral administration are slightly soluble and wettable in water, and, therefore, have very low bioavailability, which furthermore varies individually. The attempts made in the past to solve the problem by pharmaceutical techniques, e.g. micronization and addition of surface active agents, gave unsatisfactory results. It has been recently proposed to prepare compositions including slightly soluble drugs and hydrophilic, water-insoluble, but water-swellable cross-linked polymer carriers.

For example, European Pat. No. 78,430 discloses dihydropyridine derivatives adsorbed on cross-linked polyvinylpyrrolidone (abbreviated to crospovidone) together with polyvinylpyrrolidone. As illustrated in said patent, the drug incorporation in the cross-linked polymer is essentially carried out by swelling the polymer with a solution of the drug, followed by drying.

Other patents (cf. British Pat. No. 2,153,678) describe different techniques, such as for example high-energy co-grinding.

Compositions including a slightly soluble drug, an oil and a surfactant adsorbed on an inorganic porous substance are also known (European Pat. No. 0 448 091 A2).

SUMMARY

It has surprisingly been found that if a slightly water-soluble drug, an oil and a surface active agent are incorporated in a water-insoluble, but water-swellable cross-linked polymer, the drug solubilization improves in respect of that obtained by the prior art.

Furthermore, the drug solubilization can be modulated by the type of oil and surfactant used in the formulation. The present invention is, therefore, referred to a pharmaceutical composition including a water-swellable, but water-insoluble cross-linked polymer and a slightly watersoluble drug, wherein said drug is incorporated in said polymer together with an oil and a surface active agent.

DETAILED DESCRIPTION OF THE INVENTION

The following detailed description sets forth the characteristics and advantages of the pharmaceutical composition of the present invention. The three basic components of the composition of this invention are:
- a water-insoluble, but water-swellable cross-linked polymer,
- a synthetic or semisynthetic or natural oil or mixtures thereof,
- a non-ionic or cationic or anionic surface active agent.

Examples of water-insoluble, but water-swellable cross-linked polymers that can be used either alone or in combination in the process under the present invention are: cross-linked polyvinylpyrrolidone (crospovidone), cross-linked sodium carboxymethylcellulose, cross-linked β-cyclodextrin polymer, and cross-linked dextran.

Out of vegetable oils, the following may be for example used: olive oil, coconut oil, peanut oil, sesame oil, and soybean oil.

Out of synthetic oils, the following may be used: glycerol esters with fatty acids, such as Triacetin, Tributyrin, Myvacet, and Citroflex; esters of propylene glycol with lauric or caproic or caprylic acids; and the products denominated Lexol and Myritol.

Oils with analogous characteristics may also be used, such as isopropyl myristate, Cosmol, Cetiol, and Emulgir. For the purposes of the present invention, it has been found that some amphiphilic compounds, such as for example low-molecular-weight liquid polymers having solvent power, exhibit similar characteristics to the aforesaid oils in modifying the drug solubilization. Consequently, said liquid polymers will be included in the group of oils of the present invention. Said group of amphiphilic compounds may comprise e.g. polyethylene glycols (PEG), polypropylene glycols (PPG), and tetraglycols. The third essential component of the present invention is a surface active agent.

The following non-ionic surface active agents may be used: ethylene glycol stearates, propylene glycol stearates, diethylene glycol stearates, glycerol stearates, sorbitan esters (SPAN®) and polyhydroxyethylenically treated sorbitan esters (TWEEN®), aliphatic alcohols and PEG ethers, phenol and PEG ethers.

The following cationic surface active agents may be used: quaternary ammonium salts (e.g. cetyltrimethylammonium bromide) and amine salts (e.g. octadecylamine hydrochloride). The following anionic surface active agents may be used: sodium stearate, potassium stearate, ammonium stearate, and calcium stearate; triethenolamine stearate, sodium lauryl sulphate, sodium dioctylsulphosuccinate, and sodium dodecylbenzenesulphonate. Natural surface active agents may also be used, such as for example phospholipids, e.g. diacylphosphatidyl glycerols, diaceylphosphatidyl cholines, and diaceylphosphatidic acids, the precursors and derivatives thereof, such as for example soybean lecithin and egg yolk.

In the composition of this invention, the ratio by weight of oil to polymer is 0.1:100 to 2000:100, and preferably 0.5:100 to 1000:100; the ratio by weight of surface active agent to polymer is 0.1:100 to 400:100, and preferably 0.1:100 to 100:100. In any case, the weight ratio of the drug to said polymer is 0.1:100 to 1000:100, and preferably 10:100 to 100:100.

The formulation of the compositions of the invention may include other substances in addition to the three basic components mentioned above, i.e. antioxidants, complexing agents of metals, flavouring agents. etc. The drugs that may be used in the compositions of the present invention are preferably selected from those having a low solubility in water, such as for example: megestrol acetate, medroxyprogesterone acetate, cyproterone, progesterone, steroids and derivatives thereof, estriol, estradiol, estrogens and derivatives thereof, ursodeoxycholic acid, taurodeoxycholic acid, bile acids and salts and derivatives thereof, diacerein, piroxicam, tenoxicam, ibuprofen, naproxen, diclofenac, anti-inflammatory non-steroid acids, lipid-soluble benzoquinones, e.g. ubidecarenone, etoposide, temazepam and benzodiazepines, nicorandil, cyclosporins and derivatives thereof, ipriflavone and analogues thereof.

The compositions of the present invention may be prepared by known methods of drug incorporation in cross-linked polymers: the selection of a given technique instead of another does not cause significant differences in the characteristics of the final product, said characteristics being primarily a result of the presence of the three basic components (cross-linked polymer, oil and surface active agent).

A procedure for the preparation of said compositions may be as follows: the drug is dissolved in the oil by a common mixer at room or at high temperature; the resulting product is added with the surface active agent at room or at high temperature. Alternatively, the surface active agent is dissolved in the oil and the resulting product may be added with the drug; or else the drug is dissolved in the surface active agent and the resulting mixture is added to the oil. A solvent may be used on drug solubilization in the oil and/or in the surface active agent to facilitate complete drug dissolution. Should the oil and/or the surface active agent be solid, drug mixing would be carried out at a temperature exceeding the melting temperature of the other two components. The mixture consisting of drug, oil and surface active agent is then added to the cross-linked polymer by any of the known techniques. For example, the drug/oil/surface active agent mixture is added to the cross-linked polymer in an agitated reactor or in a rotary evaporator or in a granulating drum, or said mixture is sprayed in a fluidized bed consisting of the polymer in suspension in an air flow. The polymer used is in powder form with particle size of 0.1 to 200 µm.

Incorporation of the drug/oil/surface active agent mixture in the polymer may be conducted at a temperature higher than the melting temperature of one or more components, including the drug. When the drug/oil/surface active agent mixture is prepared in the presence of a solvent, this is removed—after the mixture incorporation in the polymer—by any of the drying methods commonly used in pharmaceutical practice. As apparent to those skilled in the art, modifications to the techniques of preparation of said mixture and of addition of same to the cross-linked polymer may be effected without departing from the scope of this invention, since they do not affect the composition of the final product. Therefore, the present invention is also referred, e.g., to a procedure envisaging addition of the drug alone to the cross-linked polymer (by swelling with solution, co-grinding, co-melting, etc.), followed by addition of the oil/surface active agent mixture; or a procedure envisaging addition of the oil and surface active agent, followed by addition of the drug; or a combination of the aforesaid procedures.

Finally, it is to be pointed out that the composition in powder form as obtained from the procedures mentioned above may be coated with a polymeric film further to adjust the rate of drug release. For example, should the drug be released in the intestinal tract, it would be coated with a polymer passing through the stomach unaltered, e.g. an acrylic polymer; or, should release be sustained and bioavailability be high, coating would consist of a controlled-release polymer, e.g. ethylcellulose.

Alternatively, said composition in powder form may be mixed with gelling polymer powders, e.g. hydroxypropylmethylcellulose, xanthane, etc. and the resulting mixtures may be compressed to obtain controlled release matrices.

EXAMPLE 1

A solution of 5.5% temazepam and PEG 400 was added to 1 g crospovidone having granule size of 0.1 to 200 µm, so as to secure a drug/polymer ratio equal to 1:20 by weight. Said solution was slowly added to crospovidone in a granulating drum at room temperature. The resulting mixture was allowed to stand at room temperature for 24 hrs.

EXAMPLE 2

A mixture of 2.27 g temazepan and 22.73 g crospovidone was fed to a high-energy colloid mill and ground for 2 hrs. The ground mixture was added, according to Example 1, with a Citroflex (triethyl citrate) solution containing 20% Tween 80, so as to secure a mixture/solution ratio equal to 1:1 by weight.

EXAMPLE 3

Ubidecarenone (2 g) was dissolved in a 50% mixture (6 g) of Lexol PG 865 (propylene glycol dicaprilate/dicaprate) and Tween 80. Following the procedure of Example 1, the obtained solution was added, at 50° C., to crospovidone (3 g), so as to secure a drug/polymer ratio equal to 1:3 by weight. The product obtained was allowed to stand at room temperature for 24 hrs.

EXAMPLE 4

Following the procedure of Example 1, a solution of 20% ubidecarenone and Cosmol 525 (neopentyl glycol ethyl hexanoate) was added, at 50° C., to crospovidone (1 g), so as to secure a drug/polymer ratio equal to 1:5 by weight.

EXAMPLE 5

A mixture of 5.25 g etoposide and 15.75 g crospovidone was fed to a high-energy colloid mill and ground for 30 min. The ground mixture was added, according to Example 1, with a triacetin solution containing 20% Tween 80, so as to secure a mixture/solution ratio equal to 1:0.35 by weight.

EXAMPLE 6

Etoposide (5.25 g) and crospovidone (15.75 g) were co-ground according to Example 2. The product obtained was added, according to Example 1, with a solution of PEG 400 containing 20% Tween 80, so as to secure a ground mixture/solution ratio equal to 1:0.35 by weight.

EXAMPLE 7

A solution of 8% nicorandil and triacetin was added to crospovidone (1 g) according to Example 1, so as to secure a drug/polymer ratio equal to 1:12.5 by weight.

EXAMPLE 8

A solution of nicorandil (6%) in a 1:1 triacetin-Lexol mixture was added to crospovidone according to Example 1, so as to secure a drug/polymer ratio equal to 1:5 by weight.

EXAMPLE 9

A mixture of 3.3 g nifedipine and 16.7 g crospovidone was fed to a high-energy colloid mill and ground for 3 hrs. The ground mixture was added, according to Example 1, with a Citroflex solution containing 15% Tween 20, so as to secure a mixture/solution ratio equal to 1:0.2 by weight.

EXAMPLE 10

Crospovidone powder added with nifedipine and mixed with Citroflex/Tween 20 according to Example 9 was added with colloidal silica (1%), compressed and granulated by an oscillating granulator. The granulated product obtained was suspended in a fluidized bed column and coated by spraying with an ethanol/water solution of acrylic polymer, Eudragit S100 (acrylic polymer/granulated material ratio equal to 0.3:1 by weight). After spraying, the product was dried.

EXAMPLE 11

Crospovidone powder (250 g) added with nifedipine and mixed with Citroflex/Tween 20 according to Example 9 was added with 200 g methylcellulose (Methocel ARC) and 5 g colloidal silica (Aerosil 200). After mixing, 50 g xanthane (Satiaxane CX 91) and magnesium stearate (5 g) were added. After further mixing, the powder was compressed in 19×8 mm moulds.

EXAMPLE 12

A mixture of 2.5 g piroxicam and 22.5 g crospovidone was ground according to Example 9 for 4 hrs. The ground mixture was added with a triacetin solution containing 20% Tween 60, so as to secure a ground mixture/solution ratio equal to 1:0.5 by weight.

EXAMPLE 13

A mixture of 2.5 g piroxicam and 22.5 g cross-linked β-cyclodextrin was ground according to Example 9. The ground mixture was added with a PEG 400 solution containing 15% Tween 60, so as to secure a ground mixture/solution ratio equal to 1:0.5 by weight.

EXAMPLE 14

A mixture of 4 g ipriflavone and 20 g crospovidone was ground according to Example 2. The ground mixture was added, according to Example 1, with a Myritol 318 solution containing 15% Tween 20, so as to secure a ground mixture/solution ratio equal to 1:0.5 by weight.

EXAMPLE 15

PVP-C1 (8.10 g) and a solution (30 ml) of nifedipine and methylene chloride (90 mg/ml) containing Tween 80 (4.5 mg/ml) were put in a mortar. After complete imbibition, the mixture was fed to a vacuum oven at 30° C. for 8 hrs and added with triacetin, so as to secure a triacetin/solid mass ratio equal to 0.5:1 by weight. After 24 hrs the powder was crushed in the mortar and sieved through 1 mm sieve.

COMPARATIVE EXAMPLES BY THE PRIOR ART

EXAMPLE A

Example 5 was repeated without addition of triacetin and Tween 80.

EXAMPLE B

Example 3 was repeated without addition of Lexol PG 865 and Tween 80.

EXAMPLE C

Example 3 was repeated but crospovidone was substituted with high-surface-area porous silica (GRACE 5).

EXAMPLE D

Example 3 was repeated but crospovidone was substituted with low-surface-area porous silica (GRACE 7).

COMPOSITIONS CHARACTERIZATION

The compositions obtained as per the Examples under the present invention and according to the prior art were characterized as far as concerns the solubilization kinetics, dissolution rate, and plasma levels in vitro. The results obtained with compositions containing etoposide and ubidecarenone are described below.

Etoposide a) Solubilization kinetics

FIG. 1 is a graphic representation of etoposide solubilization kinetics curves (compositions of Examples 5, 6, and A). Solubilization was measured by taking samples at very short intervals from a buffer solution at pH 5.5, 37° C., under constant oversaturation conditions. The Figure clearly shows an improved kinetics of release from the compositions of the invention, resulting in an increased drug availability even over prolonged times. It is also apparent that the drug release characteristics may be effectively modulated by the type of oil used, e.g. triacetin (Example 5) and PEG (Example 6).

b) Dissolution rate

FIG. 2 is a graphic representation of release curves under sink conditions (900 ml; 37° C; 100 rpm) referred to the compositions of Examples 5 and 6, compared with the composition of Example A. As apparent from said curves, the compositions of this invention exhibit a higher dissolution rate than the composition of the prior art. Furthermore, the release profile may be modulated by the type of oil used.

Ubidecarenone a) Solubilization kinetics

FIG. 3 is a graphic representation of ubidecanerone solubilization kinetics curves under non-sink conditions (pH 7.1+1% Tween 80) (composition of Example 3 in comparison with the composition of Example B). The Figure clearly shows that the composition of the invention has improved solubility characteristics.

b) Dissolution rate

Figure 1:
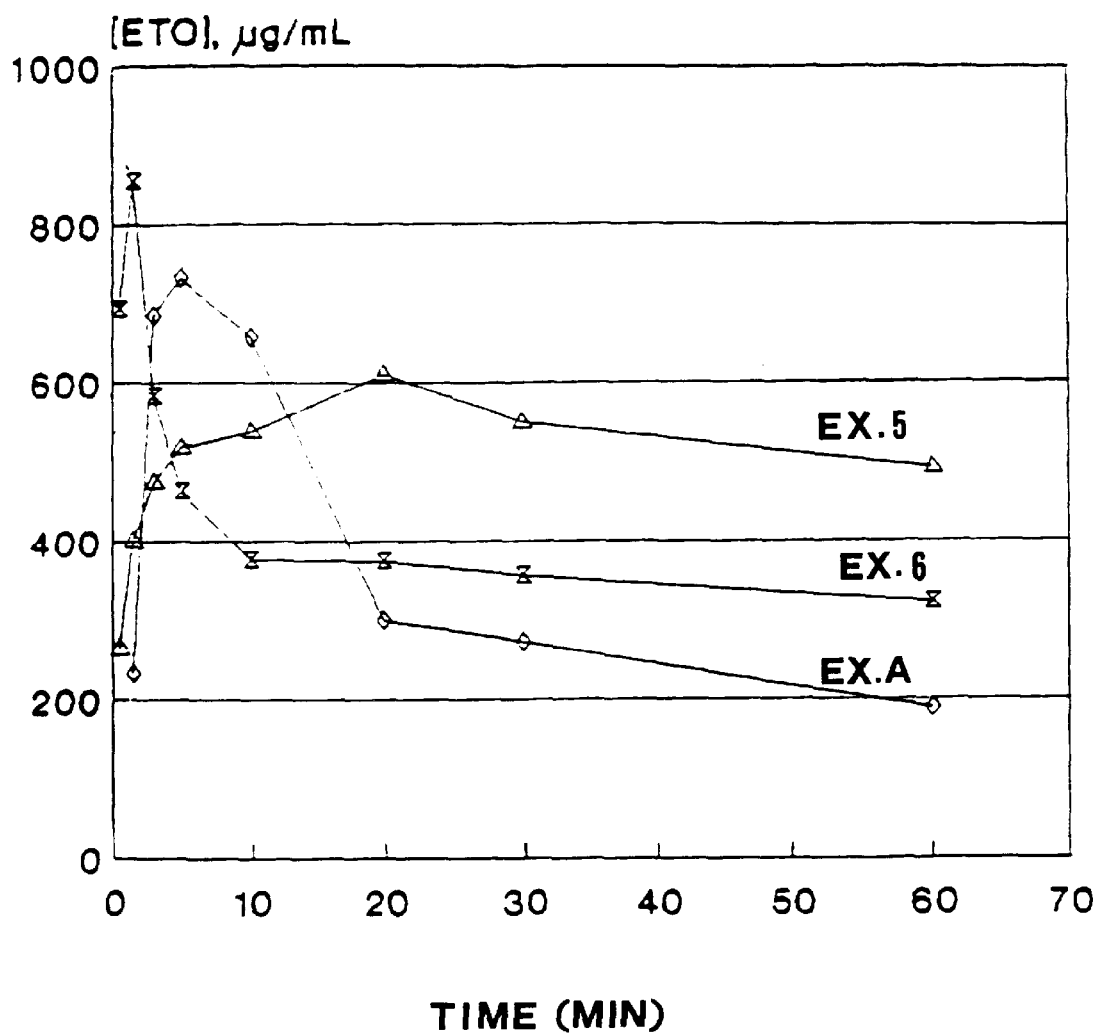
Figure 2:
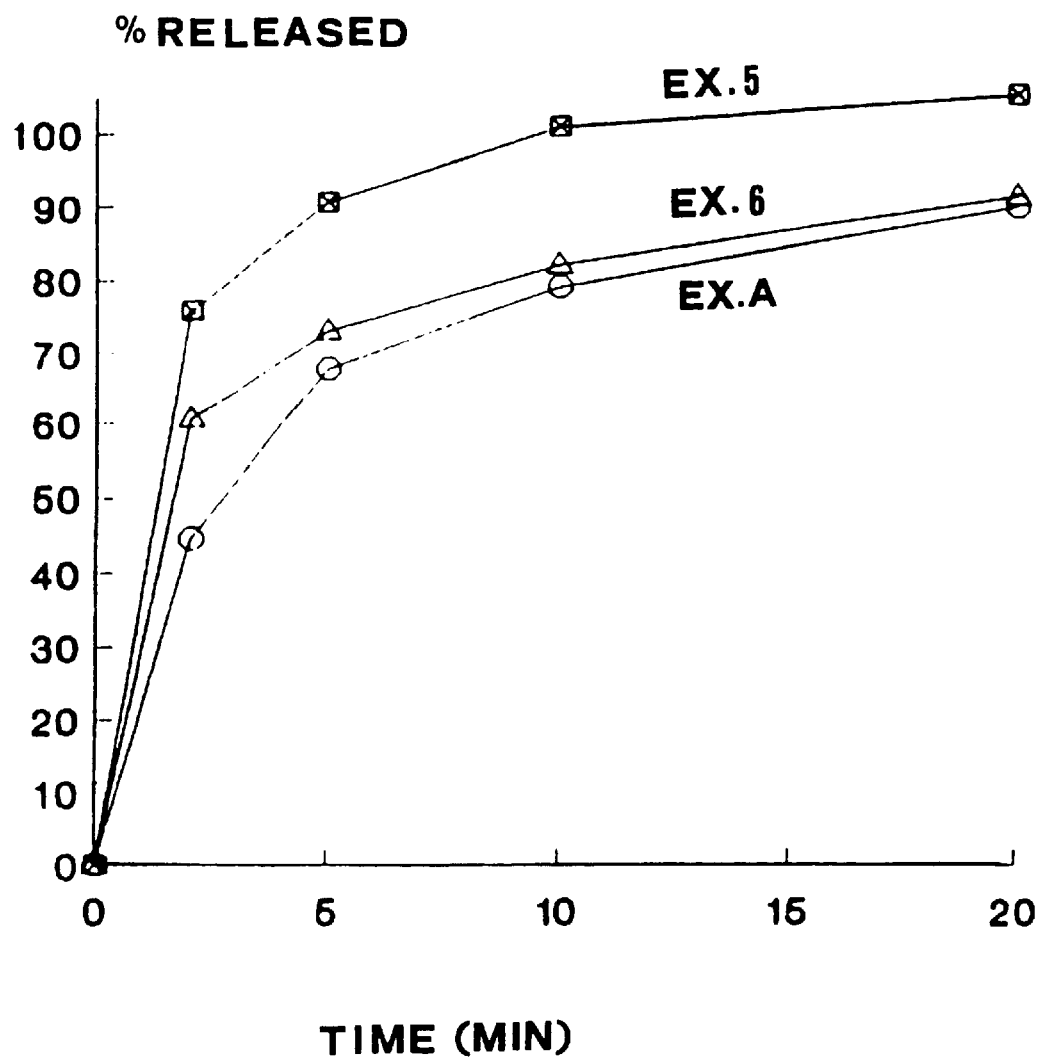
Figure 3:
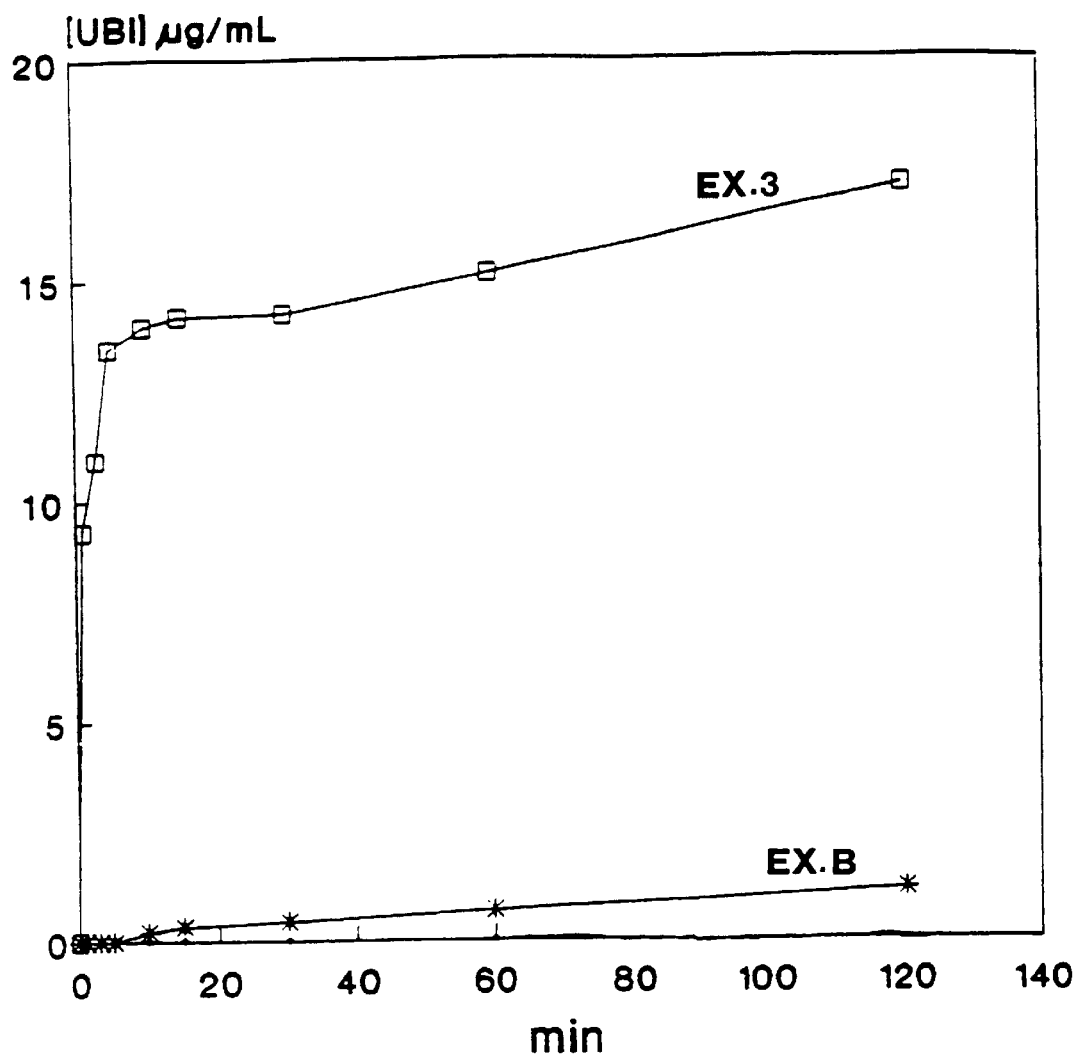
Figure 4:
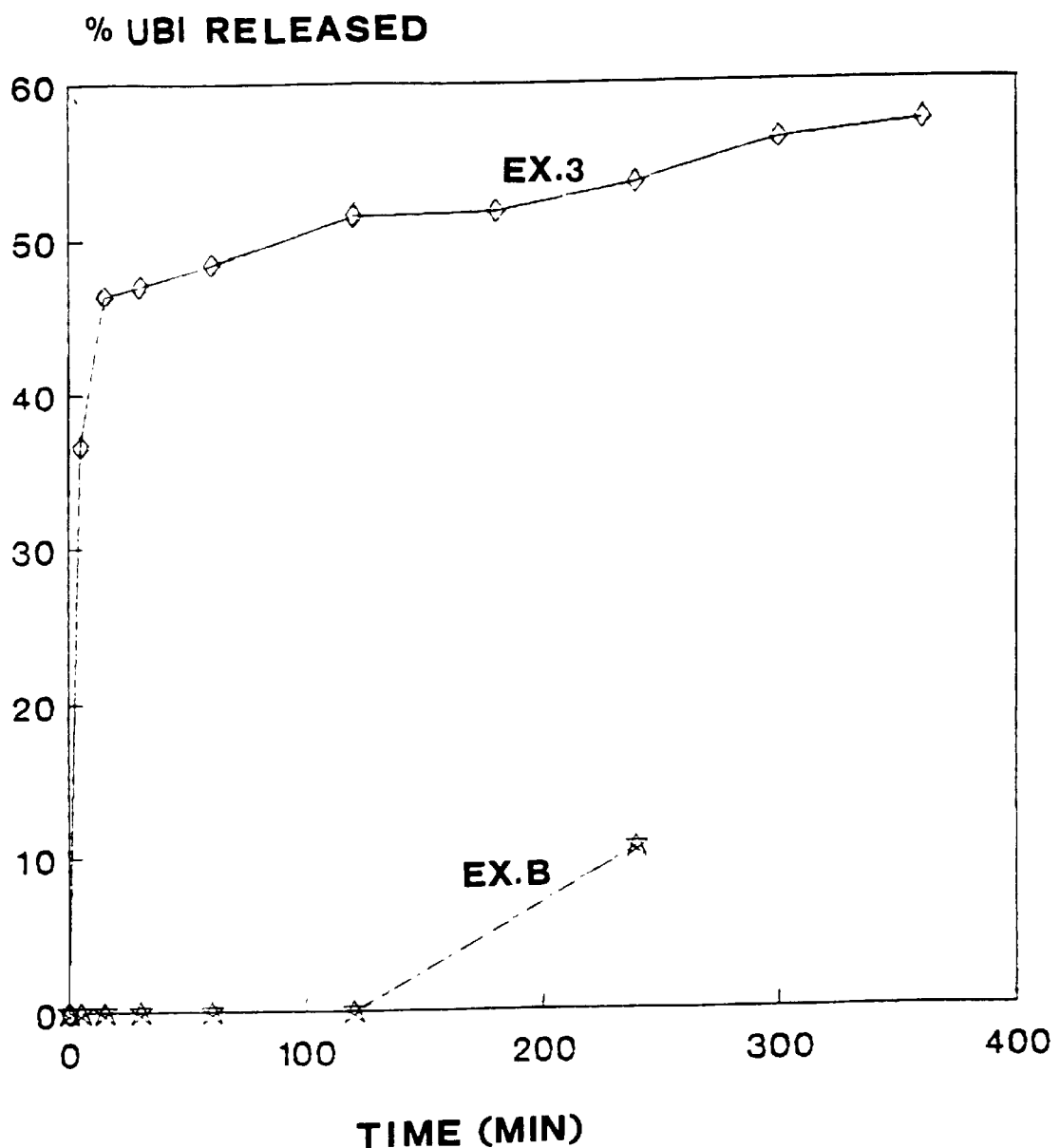
FIG. 4 is a graphic representation of ubidecarenone release curves under sink conditions (ph 7.5+1% Tween 80) (composition of Example 3 in comparision with the composition of Example B). In this case too, the release from the composition of the invention is decidedly superior to that of the prior art.
Figure 5:
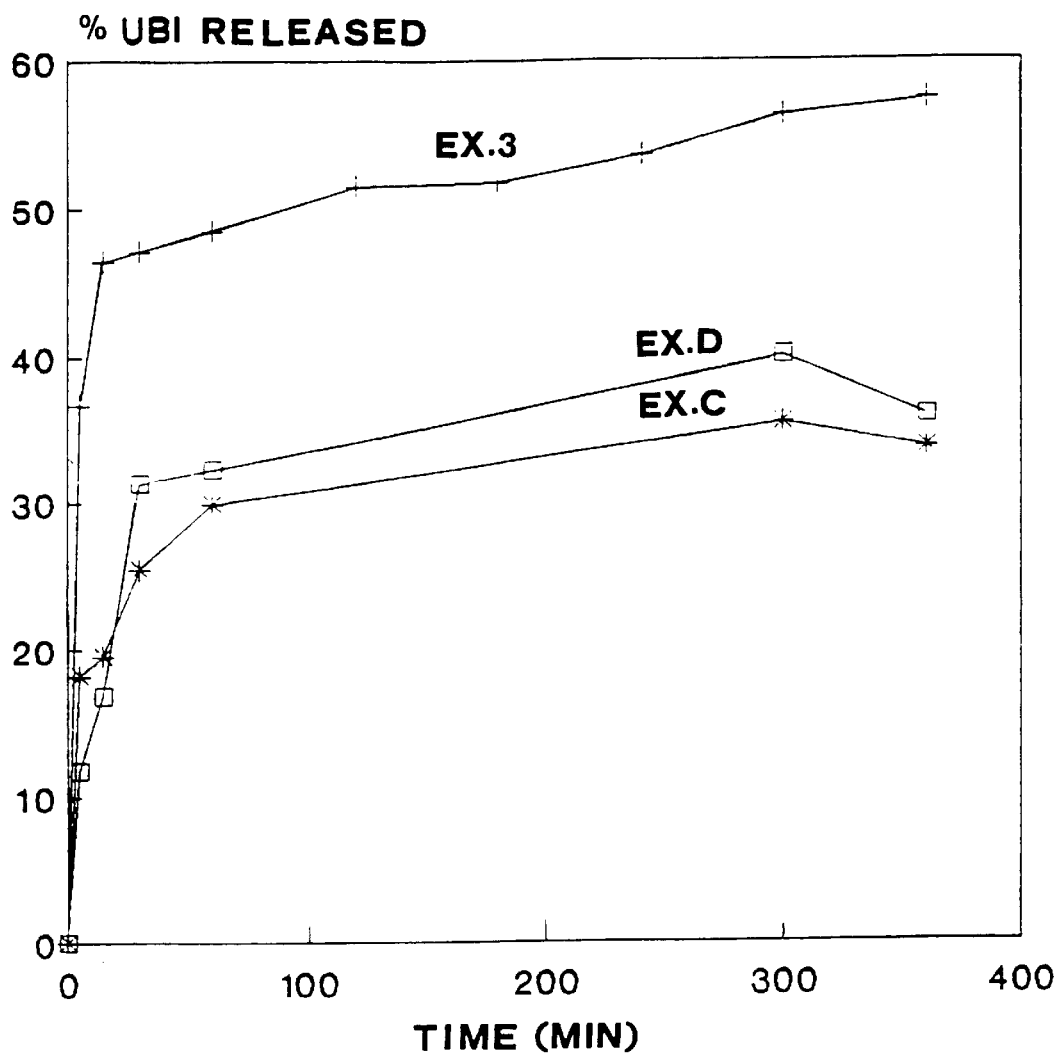
FIG. 5 is a graphic representation of the dissolution data of the preparation of Example 3 compared with the preparations using silica (Examples C and D). In this case too, the composition of this invention is decidedly superior.
Figure 6:
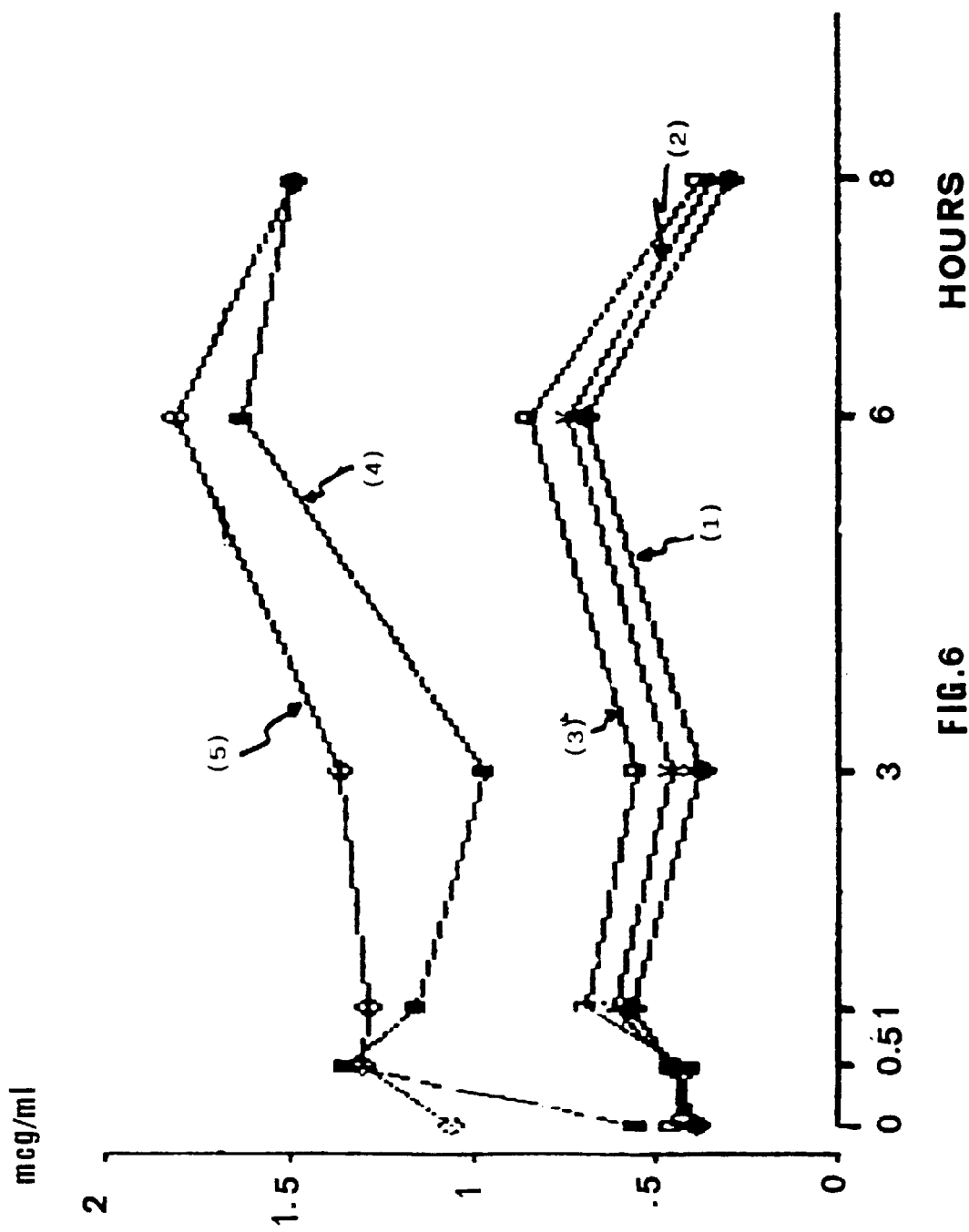

c) FIG. 6 is a graphic representation of ubidecarenone plasma levels achieved by dogs (beagle) after administration of a single dose (50 mg), repeated 7 days after, of the composition of the invention (Example 3), in comparison with the levels of a commercial composition (UBI COMM., 50 mg capsules).

The various curves represent:

Curve (1): basal plasma level;

Curve (2): plasma level after single administration of commercial composition UBI COMM.;

Curve (3): plasma level after the aforesaid repeated administration of commercial composition UBI COMM.;

Curve (4): plasma level after single administration of composition of Example 3;

Curve (5): plasma level after the aforesaid repeated administration of composition of Example 3.

As apparent from the curves of FIG. 6, the plasma levels of the composition of the invention are much higher than the plasma levels of the commercial composition. Analogous results were obtained with the products referred to in the other Examples.

What is claimed is:

1. A pharmaceutical composition having improved solubilization kinetics, dissolution rate and plasma level, said composition consisting essentially of
    a slightly water-soluble drug selected from the group consisting of etoposide, ubidecarenone, cyclosporin, progesterone, megestrol acetate and nifedipine;
    a water-insoluble polymer consisting of cross-linked polyvinylpyrrolidone;
    an oil selected from the group consisting of triacetin, tributyrin, glycerol esters with fatty acids, PEG 400, and propylene glycol dicaprilate/dicaproate; and
    a surface active agent selected from the group consisting of sorbitan esters and polyhydroxyethylenically treated sorbitan esters.

2. A pharmaceutical composition having improved solubilization kinetics, dissolution rate and plasma level, said composition consisting essentially of
    a slightly water-soluble drug selected from the group consisting of etoposide, ubidecarenone, cyclosporin, progesterone, megestrol acetate and nifedipine;
    a water-insoluble polymer consisting of cross-linked polyvinylpyrrolidone;
    an oil selected from the group consisting of triacetin, tributyrin, glycerol esters with fatty acids, PEG 400, and propylene glycol dicaprilate/dicaproate; and
    a surface active agent selected from the group consisting of sorbitan esters and polyhydroxyethylenically treated sorbitan esters, and wherein the weight ratio of said drug to said polymer is from 0.1:100 to 1000:100, the weight ratio of said oil to said polymer is from 0.5:100 to 1000:100, and the weight ratio of said surface active agent to said polymer is from 0.1:100 to 100:100.

3. A pharmaceutical composition having improved solubilization kinetics, dissolution rate and plasma level, said composition consisting essentially of
    a slightly water-soluble drug selected from the group consisting of etoposide and ubidecarenone;
    a water-insoluble polymer consisting of cross-linked polyvinylpyrrolidone;
    an oil selected from the group consisting of triacetin, PEG 400, and propylene glycol dicaprilate/dicaproate; and
    a surface active agent consisting of polysorbate 80.

4. A pharmaceutical composition having improved solubilization kinetics, dissolution rate and plasma level, said composition consisting essentially of
    a slightly water-soluble drug selected from the group consisting of etoposide and ubidecarenone;
    a water-insoluble polymer consisting of cross-linked polyvinylpyrrolidone;
    an oil selected from the group consisting of triacetin, PEG 400, and propylene glycol dicaprilate/dicaproate; and
    a surface active agent consisting of polysorbate 80, and wherein the weight ratio of said drug to said polymer is from 0.1:100 to 1000:100, the weight ratio of said oil to said polymer is from 0.5:100 to 1000:100, and the weight ratio of said surface active agent to said polymer is from 0.1:100 to 100:100.

* * * * *